(12) United States Patent
Ferro

(10) Patent No.: US 10,568,646 B2
(45) Date of Patent: Feb. 25, 2020

(54) SURGICAL METAL DEBRIS REDUCTION SYSTEM

(71) Applicant: AOD Holdings, LLC, Arroyo Grande, CA (US)

(72) Inventor: Thomas D. Ferro, Arroyo Grande, CA (US)

(73) Assignee: AOD HOLDINGS, LLC, Arroyo Grande, CA (US)

( * ) Notice: Subject to any disclaimer, the term of this patent is extended or adjusted under 35 U.S.C. 154(b) by 736 days.

(21) Appl. No.: 15/261,248

(22) Filed: Sep. 9, 2016

(65) Prior Publication Data

US 2017/0071612 A1 Mar. 16, 2017

Related U.S. Application Data

(60) Provisional application No. 62/217,297, filed on Sep. 11, 2015.

(51) Int. Cl.
  *A61B 17/17* (2006.01)
  *A61B 17/16* (2006.01)
  *A61B 17/58* (2006.01)
  *A61B 17/90* (2006.01)

(52) U.S. Cl.
  CPC .......... *A61B 17/17* (2013.01); *A61B 17/1637* (2013.01); *A61B 17/58* (2013.01); *A61B 2017/90* (2013.01)

(58) Field of Classification Search
  CPC . A61B 17/17; A61B 17/1703; A61B 17/1732; A61B 17/175; A61B 17/1764
  See application file for complete search history.

(56) References Cited

U.S. PATENT DOCUMENTS

| 5,514,140 A * | 5/1996 | Lackey | A61B 17/155 606/80 |
| 5,735,856 A * | 4/1998 | McCue | A61B 17/155 606/87 |
| 6,344,043 B1 * | 2/2002 | Pappas | A61B 17/155 606/79 |
| 8,075,592 B2 * | 12/2011 | Landry | A61B 17/1604 606/246 |
| 8,398,645 B2 * | 3/2013 | Aker | A61B 17/155 606/88 |
| 8,496,663 B2 * | 7/2013 | White | A61B 17/155 606/88 |
| 2011/0144766 A1 * | 6/2011 | Kale | A61B 17/686 623/23.63 |

* cited by examiner

*Primary Examiner* — Anu Ramana
(74) *Attorney, Agent, or Firm* — McDonnell Boehnen Hulbert & Berghoff LLP

(57) ABSTRACT

A surgical metal debris reduction system is provided for use in orthopedic surgical procedures having a metal block with one or more guide openings that accept bone cutting tools or bone drilling tools. One or more non-metallic bushings are included in the system that have outer dimensions such they can be removably inserted in the guide openings and have internal dimensions sized to accept bone cutting tools or bone drilling tools such that metal on metal contact is prevented during use of the tools, thus preventing or reducing generation and deposition of metal debris within the surgical field.

7 Claims, 4 Drawing Sheets

SURGICAL METAL DEBRIS REDUCTION SYSTEM

CROSS REFERENCE TO RELATED APPLICATIONS

The present application is a non-provisional application of U.S. Provisional Patent Application No. 62/217,297, filed Sep. 11, 2015. The entire disclosure contents of this application is herewith incorporated by reference into the present application.

FIELD OF INVENTION

The present invention relates to tools or other instruments to assist surgeons during orthopedic surgical procedures, such as, knee arthroplasty. More particularly, the invention disclosed herein relates to a system of cutting guides and removable biocompatible bushings that reduce or eliminate the formation of metal debris caused by metal on metal abrasive contact.

BACKGROUND

Many orthopedic procedures involve tools or other instruments that assist the surgeon during surgery. One such instrument is the surgical cutting block, otherwise known as a cutting guide, which is used during orthopedic surgical procedures to assist the surgeon in making proper bone cuts, such that prosthetic devices can be attached to a patient's bone. Cutting guides are typically provided in the form of metal blocks that include slots, holes or other apertures that serve as precise guides that show the surgeon where the bone is to be cut or drilled.

Orthopedic surgical operations routinely call for the precise and accurate cuts of bone material. Generally, these cuts, or resections, are made using surgical saws or milling devices. These instruments, while excellent at cutting the bone material, typically require cutting guides in surgical procedures calling for accurate cuts. For example, a surgeon performing a total knee arthroplasty must make several cuts on the distal end of the femur to properly fit a prosthetic femoral component. If these resections are incorrectly made, the surgery can result in failure and require further corrective procedures. Although the cutting guides allow for precise cutting, they also unfortunately can lead to deposition within the surgical field of metal debris caused by the repetitive contact between the metal cutting guide and the metal tool being used to cut or drill into the bone. Although the surgeon will always attempt to remove as much of the metal debris as possible, inevitably metal debris will remain within the patient after surgery. Recent evidence now points to the possible conclusion that this remaining metal debris may be more detrimental to the patient than originally believed.

With the above in mind, there is a compelling need to reduce or eliminate metal debris during orthopedic surgical procedures. As described in detail below, the presently disclosed invention provides systems of metal cutting guides and removable, disposable bushings made of biocompatible materials that reduce or eliminate the formation of metal debris by avoiding metal on metal contact.

SUMMARY

As mentioned, this disclosure is directed to an assembly or system for use in an orthopedic surgical procedure to reduce or eliminate metal debris production in a patient, the assembly may comprise a metal block having a guide opening configured to accept a bone cutting tool or a bone drilling tool and a non-metallic bushing having outer dimensions such that the bushing can be removably inserted into the guide opening. In some cases, the metal block can contain a plurality of guide openings, where at least one guide opening is non-circular and configured to accept a non-circular bushing that has an internal configuration and dimension that will accept a bone saw blade or like cutting tool. Preferably, the system contains a number of bushings, each having the same external dimensions such that each fits into a specific guide opening, however, the internal dimensions of each are different such that different sized saw blades are matched or correspond to the different internal dimensions. Alternatively, the internal dimensions are each different such that a single sized saw blade will fit into each of the bushings but the different internal dimensions are configured such that the saw blade is guided in a different orientation or angle for each different bushing.

The metal block of the assembly disclosed herein can also have a plurality of guide openings that are circular and configured to accept a circular non-metallic bushing that has an internal dimension that will accept a bone drill. Alternatively, the metal block can have non-circular guide openings that will accept a non-metallic bushing having a circular through opening. Such a bushing will allow a surgeon to use a bone drilling tool in combination with a rectangular guide opening. Regardless of whether the guide opening is circular or another shape, it is preferred that the non-metallic bushing be fabricated from a material that is bio-compatible. As used herein, biocompatible is meant to characterize a material that is compatible with living tissue or a living system by not being toxic, injurious, or physiologically reactive and not causing immunological rejection. Examples of acceptable biocompatible materials include, but not limited to, biocompatible polymers, such as, polyethylenes, polyamides, polysulfones, polyphenysulfones, polyketones (such as polyether ether ketone), polyphenylenes, polystyrenes, polyvinyls, and the like. Exemplary biocompatible ceramics can include hydroxyapatite, zirconia ceramics, alumina ceramics, calcium phosphates, and the like.

Concerning the fit of the bushing with the guide openings, preferably the outer dimensions of the bushing is of a size such that the bushing must be inserted into the guide opening by application of a pressing force exerted by a tool that results in a press fit. In other words, the tolerance between the outer diameter of the bushing and the guide opening could be from 0.00 in. to 0.004 in. Although such a press fit secures the bushing against relative movement with the metal block, the bushing is removable, typically through application of a force equal or greater than, in the opposite direction, of the insertion force. Again, a hand held tool may be used to apply the necessary removal force to detach the bushing from the metal block. This tool may be the same tool used to insert the bushing into the guide opening. As such, it may be desirable to include such a tool or tools as part of the assembly disclosed herein.

The assembly described herein may contain at least two bushings each having the same outer dimensions, where a first bushing has an internal opening sized to accept a first drilling tool, where the second bushing has an internal opening sized to accept a second drilling tool, wherein the size of the internal opening of the first bushing is different than the size of the second bushing. Alternatively, the size of the internal opening may be the same, but the orientation of the hole can be different to allow for a different drilling angle. In some instances, the drilling tool has a protective sleeve sized to fit over the outside diameter of the drilling tool. Preferably, in those cases, the protective sleeve is adjustable and configured to fit over the outside diameter to allow rotation of the drilling tool relative to the protective sleeve. In this way the drilling tool will not impinge or contact the guide opening during use. The protective sleeve can be formed a tube of biocompatible material or as an over molded covering or as a heat shrinking sleeve. The sleeve can also be configured such that it can easily be cut to adjust the length, thus providing a convenient means of indicating a predetermined depth of the hole to be drilled.

In some cases, it is desirable to incorporate an orientation component into the configuration of the bushing. This orientation feature can be keyed to the metal block to ensure that the correct bushing is used in the correct guide opening. Likewise, the orientation feature assists the surgeon in placing the bushing in the guide opening at the correct orientation relative to the metal block. This orientation component can be integral to the bushing, meaning that the orientation component is made of the same material as the bushing and being formed as part of process of manufacturing the bushing, such as through a co-molding process. Alternatively, the orientation component can be physically attached to the bushing as a separate stand-alone part. Attachment can be accomplished through an adhesive, laser or thermal welding, or a mechanical fastener, such as a screw or snap fit feature. The orientation component may be a projection that is configured to engage and mate with a corresponding orientation feature associated with the guide opening when the bushing is inserted into the guide opening. Further, the orientation feature can be configured to provide a surface that can be engaged in order to insert or remove the bushing from the guide opening. For example, the above-mentioned tools may be designed to engage the surface of the orientation component in order to supply the necessary force to either insert or remove the bushing from the metal block.

The features, functions, and advantages that have been discussed can be achieved independently in various embodiments or may be combined in yet other embodiments, further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Figure 1:
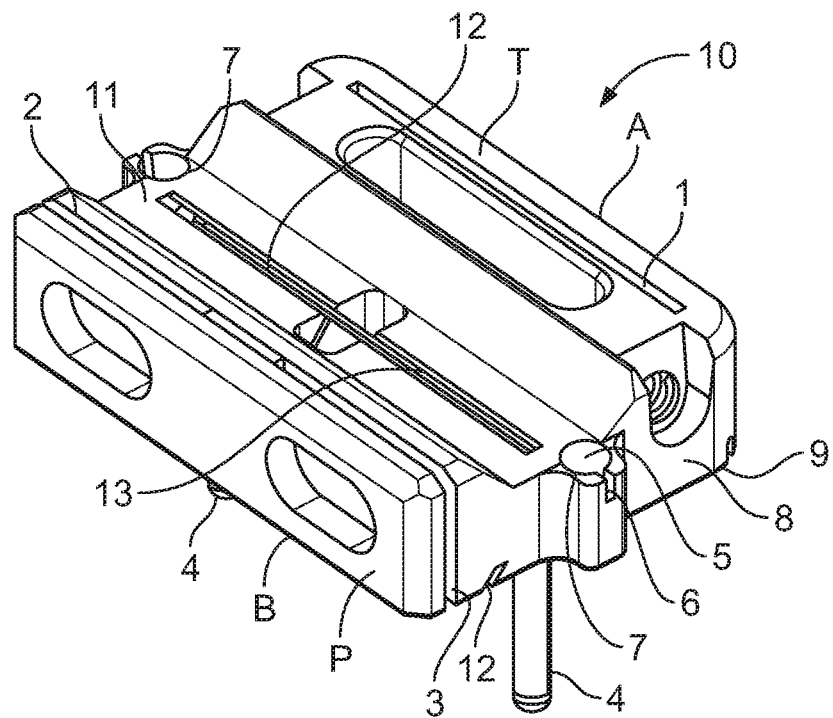
FIG. 1 shows a perspective view of the metal block of the instant disclosure containing one or more guide openings.

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Reference is now made to FIGS. 1-6. Starting with FIG. 1 there is shown a metal block 10 that is representative of any number of orthopedic surgical cutting guides, jigs, templates, and the like devices that are employed by surgeons to cut and drill bone during surgical procedures to implant artificial joints, such as in a partial knee replacement procedure. Cutting guides are generally formed from a single block of material comprised of stainless steel and/or titanium or other materials used in the art. When forming the cutting guide, the block of stainless steel/titanium material is cut or otherwise shaped to provide the desired cutting slots 1, 2, 3, 12, & 13 or drill holes 7, or other features for the block. The cutting slots 1, 2, 3, 12 & 13 are all through slots and typically configured to receive a bone cutting tool, such as a reciprocating surgical saw, and to orient the cutting tool for the surgical procedure. The metal block or surgical cutting guide 10 has at least one body portion 8 that includes a bone engaging surface 9. Body portion 8 can also include fastening pins 4 that are inserted in pre-drilled holes in the bone to stabilize and hold the metal block 10 in position during the surgical procedure.

Holes 7 of metal block 10 are through holes, meaning that opening 5 has a corresponding opening on the bone engaging surface 9. In other words, if a drill tool were inserted and pushed into holes 7, the drill would contact bone. Hole 7 is sized with opening 5 to allow insertion of bushings of the type illustrated in FIG. 2A. In a like manner the cutting slots 1, 2, 3, 12 & 13 provide access to the bone by a cutting tool and are configured to accept bushings of the type illustrated FIGS. 2B and 2C. Cutting slot 12 is a posterior chamfer cutting guide that is angled from the top T towards the bottom B posterior P. Cutting slot 13 is an anterior chamfer cutting guide that is angled from the top T towards the bottom B anterior A (see FIG. 2D).

Figure 2A:
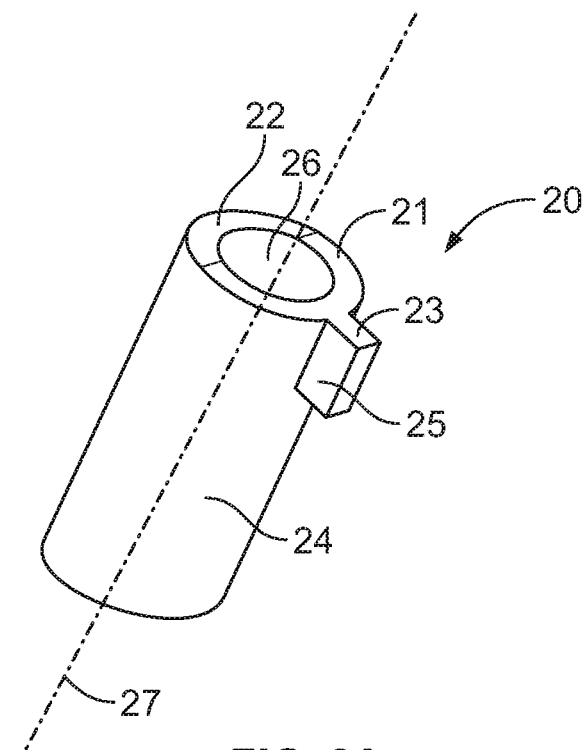
FIG. 2A shows a perspective view of a bushing of the instant disclosure configured for use with the metal block of FIG. 1 and a bone drilling tool of FIG. 6.

Turning first to bushing 20 of FIG. 2A, this bushing is cylindrical in shape having an outer wall 24 and inner opening 26 having a smaller diameter than outer wall 24. This difference defines the wall thickness 21. In some cases, it is beneficial to have a plurality of bushings 20 with identical outer diameters and varying inner opening diameters such that each bushing has a different wall thickness 21. Additionally, the inner opening diameter can vary along the longitudinal axis of bushing 20 thereby allowing different angles of orientation of an inserted drilling tool relative to the longitudinal axis 27 of the hole 7. The exposed surface 22 of bushing 20 may also be angled to accommodate and/or follow the contours of the outer surface 11 of the metal block. This is best viewed in FIG. 3 where the bushing 20 is inserted into hole 7 of metal block 10.

Figure 3:
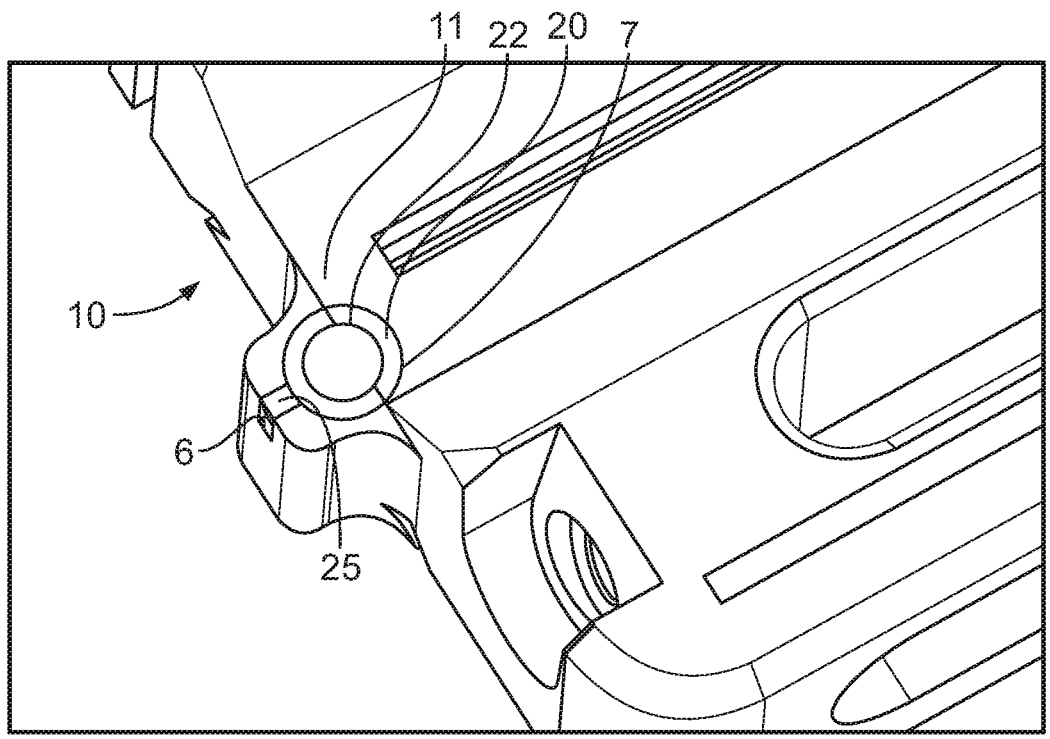
FIG. 3 shows a close-up perspective partial view of metal block of FIG. 1 having the bushing of FIG. 2A inserted into a guide opening of the metal block.

Bushing 20 can also have one or more orientation components 25. These orientation components assist in the placement and/or removal of the bushing into the metal block, for example, by allowing component 25 to engage and fit into a correspondingly shaped feature 6. This engagement is similar to a key and lock engagement. This key and lock relationship can also function as a coding feature to ensure that the correct bushing is used in the correct guide opening. Although the embodiment shown in FIG. 3 illustrates a male orientation feature 25 engaged with a female feature 6, this could be reversed. In other words, the orientation feature of the bushing 20 could be female and the corresponding feature in the metal block 10 could male. The orientation feature 25 could also have a surface 23 configured to be engaged by an insertion or removal tool, such as the exemplary tools illustrated in FIGS. 4 and 5.

Figure 2B:
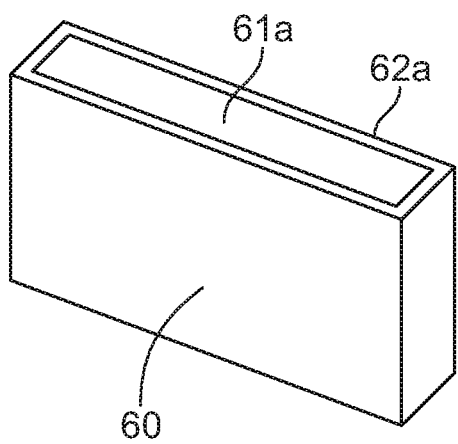
FIG. 2B shows a perspective view of an alternate bushing of the instant disclosure configured for use with the metal block of FIG. 1 and a bone cutting tool.
Figure 2C:
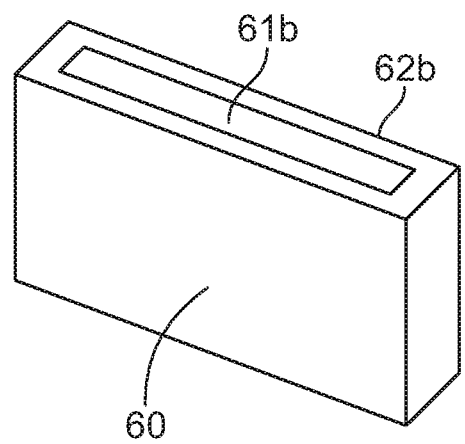
FIG. 2C shows a perspective view of yet another bushing of the instant disclosure configured for use with the metal block of FIG. 1 and a bone cutting tool.
Figure 2D:
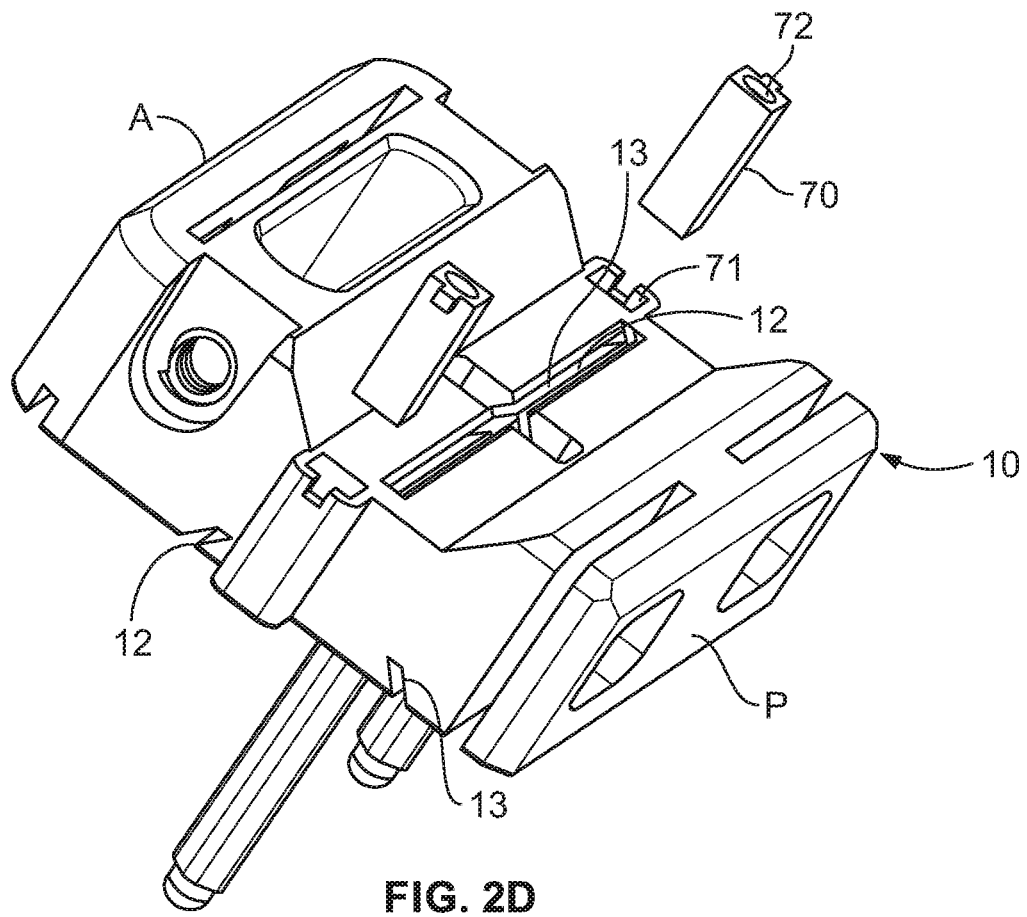
FIG. 2D shows a perspective view of yet another possible metal block and bushing combination of the instant disclosure configured for use with a bone cutting tool of FIG. 6.

FIGS. 2B, 2C & 2D illustrate another type of bushing 60 that can be used in the instant system. As opposed to the round or oval shape of bushing 20, bushing 60 is square or rectangular shaped and is configured to fit into cutting guide slots 1, 2, 3, 12 or 13. Bushing 70 has non-circular outer dimensions and is configured to fit into non-circular guide opening 71. Bushing 70 has a circular through hole 72 that can accept a bone drilling tool. Such bushings will allow a surgeon to use a bone drilling tool in combination with a rectangular guide opening and will avoid metal on metal contact.

Preferably a number of bushings 60, 70 are available for use with the presently described assembly, where each bushing 60 has the same outer dimensions and configuration, such that they can be forced fit into the same cutting slot 1, 2, 3, 12 or 13. The inner dimensions 61a, 61b are defined by wall thickness 62a, 62b, respectively. Compare FIGS. 2B and 2C. Although the outer dimensions of bushings 60 maybe the same, the inner dimensions vary from bushing to bushing so that different sized cutting tools may be used for each bushing. Alternatively, the internal dimensions can be the same to fit a single cutting tool, but relative angle of the opening can be varied to achieve different cutting angles. In all cases, the use of the bushing 60 will prevent metal on metal contact between the cutting tool and metal block 10. Likewise, a set of bushings 70 can be provided, each having the same outer dimension, but with varying internal through hole diameters. In all cases, the use of non-metallic bushings prevents metal on metal contact, which will significantly reduce the formation of metal debris that will remain in the patient after completion of the surgical procedure.

As mentioned, the bushing of the instant system disclosed herein are preferably configured both dimensionally and by choice of biocompatible materials such that they can be force fit into the one or more of the guide openings. In this fashion, the bushing will absorb the abrasion and wear of use during bone cutting and/or drilling as opposed to metal block 10. As such, it would be possible to reuse the metal block with a new set of bushings. Additionally, the guide openings in the metal block can be initially dimensioned in more of general or generic sizes, a so called "one fits all" metal block. As described above, a variety of bushings can them be provided in the assembly with varying internal dimensions (same external dimensions) such that the surgeon can select the approximately sized bushing to meet an individual patient's surgical requirements. Moreover, because the bushings are preferably only friction or force fitted into the guide openings, the used bushings can be removed and discarded after use. This allows the metal block to be re-sterilized and used in subsequent surgical procedures with a new set of varying sized bushings. The system can then be re-packaged in materials that lend themselves to being produced and distributed in "factory" (off site from the hospital or ASC (ambulatory surgical center)) sterilized sealed packages providing a higher level of sterility (ethylene oxide gas sterilization or gamma irradiation, for example, performed in/through hermetically sealed containers, provide far superior sterility compared to hospital autoclave systems) and increased convenience/economy/efficiency to the end user.

Figure 4:
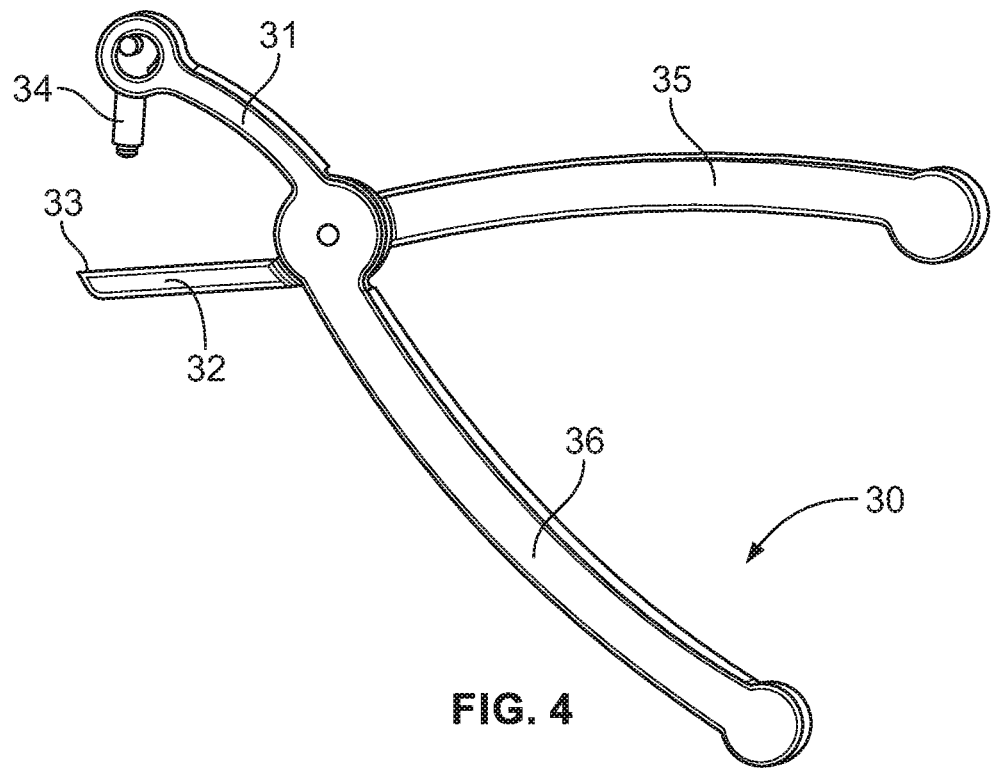
FIG. 4 shows a perspective view of a bushing insertion tool.
Figure 5:
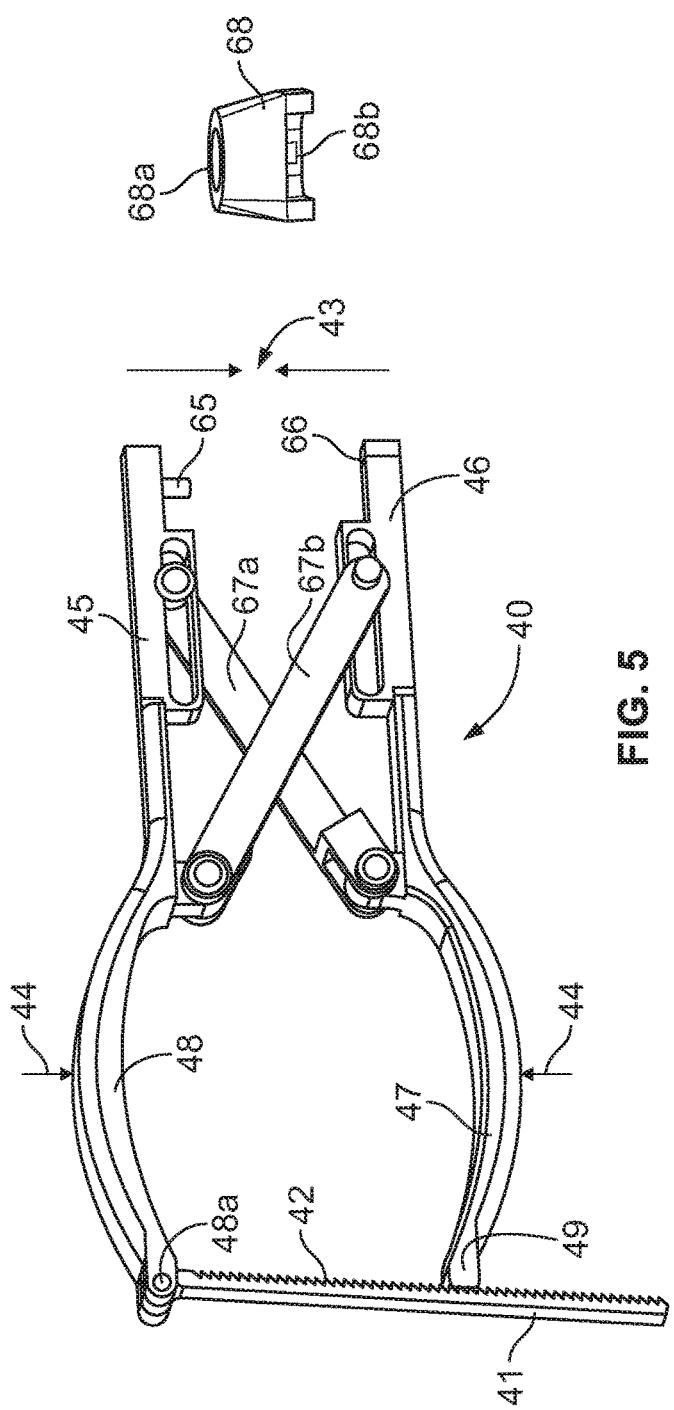
FIG. 5 shows a perspective view of bushing insertion tool along with one possible embodiment of a replaceable jaw configured for use with the bushing insertion tool for bushing removal.

FIGS. 4 and 5 present two possible tools for use with the bushings of the herein described system. FIG. 4 presents one possible bushing insertion tool 30 having handles 35 and 36 pivotally connected to jaws 31 and 32. Insertion tool 30 is configured to operate like conventional pliers or scissors where squeezing the handles 35 and 36 together causes jaws 31 and 32 to likewise close towards each other. In operation, bearing surface 33 of jaw 32 is placed in an abutting position adjacent to bone engaging surface 9. This bearing surface 33 can be configure with a special shape so that it fits into a corresponding shape in the bone engaging surface 9. This would provide an alignment guide for the tool 30. In some cases, a magnet can be used in either the bone engaging surface of the bearing surface 33 to allow correct position of the insertion tool. Insertion tip 34 is then used force bushing 20 into hole 7 of metal block 10 by exerting a downward directed force towards bearing surface 33. FIG. 5 illustrates another embodiment of a bushing insertion/extraction tool 40 that can be used to insert or remove a friction fitted bushing, such as bushing 20, from guide openings in a metal block. Tool 40 operates in an opposite manner compared to tool 30 in that movement of handles 48 and 47 in direction 44 causes jaw holder 45 and jaw 46 to close in direction 43, whereby bearing surface 66 can abut bone engaging surface 9 allowing insertion tip 65 to force bushing 20 into hole 7 of metal block 10 by exerting a downward directed force. This is achieved by tracks or a plurality of hinges 67a, 67b connecting the two handles. The insertion tip 65 can also serve as an attachment peg for replaceable jaw 68, which can be connected through hole 68a. When connected replaceable jaw 68 will engage the bushing with removal nib 68b, such that when handles 48 and 47 are moved in the opposite direction of direction 44 (i.e., opened), the removal nib 68b will pull the bushing out of the force fit engagement with the guide opening. Although not necessary for operation of tool 40, there can be attached to handle 48 a guiding tool 41 having a ratchet surface 42 configured to engage with guide 49 on handle 47 to ensure that guiding tool 41 remains in alignment with pivot point 48a of handle 48 during either insertion or removal of the bushing.

Figure 6:
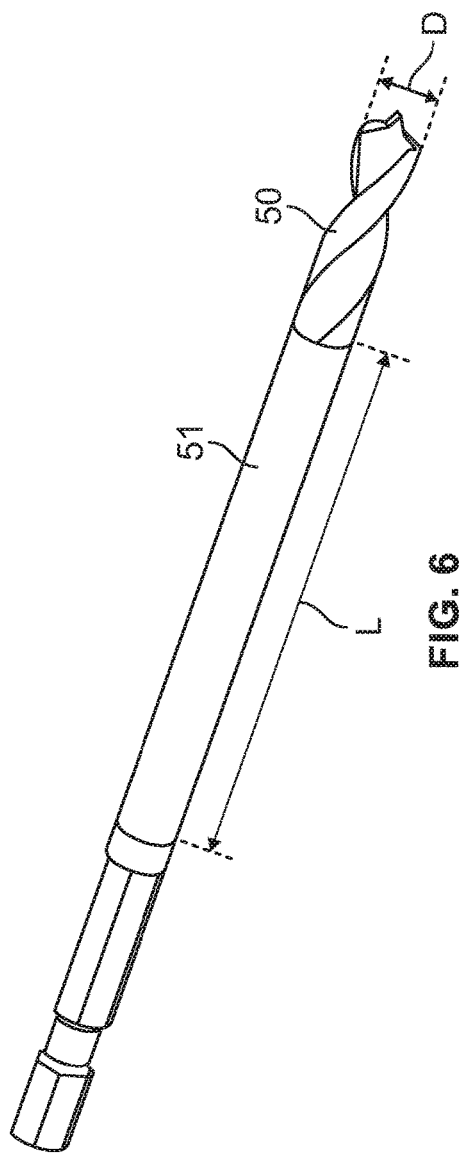
FIG. 6 shows a perspective view of a bone drilling tool having a protective covering.

FIG. 6 illustrates another possible embodiment of another type of bushing, shown as protective sleeve 51. This bushing type is configured to fit over a bone drilling tool 50 having diameter D. Like the bushing described above, protective sleeve 51 can also be constructed of a biocompatible material, such as, biocompatible polymers, including, polyethylenes, polyamides, polysulfones, polyphenysulfones, polyketones (such as polyether ether ketone), polyphenylenes, polystyrenes, polyvinyls, and the like. The length L of protective sleeve 51 can be adjusted by cutting the sleeve to a desired length such that the sleeve may serve as a depth guide to provide visual indicator to the surgeon when the desired predetermined depth of the hole being drilled has been achieved. The combination of bone drilling tool 50 and protective sleeve 51 can be used with or without bushing 20 inserted into metal block 10. Preferably, the inner diameter of protective sleeve 51 is just slightly larger than drilling tool diameter D such the protective sleeve 51 will remain stationary as the drilling tool 50 rotates relative to the protective sleeve 51. Alternatively, the protective sleeve may be heat shrunk around diameter D of the drill or over applied via an over molding process.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

The invention claimed is:

1. An assembly for use in an orthopedic surgical procedure to reduce metal debris production in a patient, the assembly comprising:
   a metal block having a guide opening configured to accept a bone cutting tool or a bone drilling tool, where the metal block comprises a bone engaging surface;
   an insertion tool comprising handles, a first jaw and a second jaw, where the first jaw comprises a bearing surface configured to abut the bone engaging surface and where relative movement of the handles causes the first jaw and the second jaw to move towards each other; and
   a non-metallic bushing comprising a bio-compatible polymer having an outside surface comprising an orientation component positioned along the outside surface and along an axis parallel to a longitudinal axis of the bushing, where outer dimensions of the bushing are of a size such that the bushing must be inserted into the guide opening by application of a pressing force on the bushing exerted by the second jaw of the insertion tool during movement of the handles,
   wherein the orientation component has a shape that matches and engages a correspondingly shaped feature located on an inner surface of the metal block that defines the guide opening such that a lock and key engagement is formed when the bushing is press fit into the guide opening using the insertion tool.

2. The assembly of claim 1 where the metal block comprises a plurality of guide openings, where one guide opening is non-circular and configured to accept a non-circular bushing that has an internal dimension that will accept a bone saw blade.

3. The assembly of claim 2 where another of the plurality of guide openings is circular and configured to accept a circular bushing that has an internal dimension that will accept a bone drill.

4. The assembly of claim 1 further comprising at least two bushings each having the same outer dimensions, where a first bushing has an internal opening sized to accept a first bone cutting tool or a first drilling tool, where a second bushing has an internal opening sized to accept a second bone cutting tool or a second drilling tool, and wherein the size of the internal opening of the first bushing is different than the size of the second bushing.

5. The assembly of claim 1 further comprising a drilling tool having an outside diameter and a protective sleeve, where the protective sleeve is adjustable and configured to fit over the outside diameter to allow rotation of the drilling tool relative to the protective sleeve.

6. The assembly of claim 1 where the orientation component is a projection from the outside surface of the bushing.

7. The assembly of claim 1 where the orientation component is configured to provide a surface configured for engagement with an insertion tip or replaceable jaw on the second jaw in order to insert or remove the bushing from the guide opening.

* * * * *